United States Patent
Yang et al.

(10) Patent No.: US 11,587,651 B2
(45) Date of Patent: Feb. 21, 2023

(54) PERSON-CENTRIC GENOMIC SERVICES FRAMEWORK AND INTEGRATED GENOMICS PLATFORM AND SYSTEMS

(71) Applicant: International Business Machines Corporation, Armonk, NY (US)

(72) Inventors: Pengwei Yang, Belmont, MA (US); Cheryl L. Eifert, Watertown, MA (US); Kirk A. Beaty, Goldens Bridge, NY (US); Fang Wang, Plano, TX (US)

(73) Assignee: MERATIVE US L.P., Ann Arbor, MI (US)

( * ) Notice: Subject to any disclaimer, the term of this patent is extended or adjusted under 35 U.S.C. 154(b) by 205 days.

(21) Appl. No.: 16/296,664

(22) Filed: Mar. 8, 2019

(65) Prior Publication Data

US 2020/0286602 A1    Sep. 10, 2020

(51) Int. Cl.
*G16H 10/60*    (2018.01)
*G06F 16/23*    (2019.01)
(Continued)

(52) U.S. Cl.
CPC ............ *G16H 10/60* (2018.01); *G06F 16/23* (2019.01); *G06F 40/279* (2020.01); *G16H 10/20* (2018.01); *G06N 20/00* (2019.01)

(58) Field of Classification Search
CPC ........ G16H 10/60; G16H 10/20; G06F 16/23; G06F 40/279; G06N 20/00
See application file for complete search history.

(56) References Cited

U.S. PATENT DOCUMENTS

2002/0052761 A1    5/2002  Fey et al.
2003/0113727 A1 *  6/2003  Girn ........................ G06Q 50/24
                                                    435/6.11
(Continued)

FOREIGN PATENT DOCUMENTS

WO    WO-0042436 A1 *  7/2000  ......... G01N 33/5005

OTHER PUBLICATIONS

Torii, Manabu et al. "Using machine learning for concept extraction on clinical documents from multiple data sources." Journal of the American Medical Informatics Association, vol. 18, Issue 5, Sep. 2011, pp. 580-587. (Year: 2011).*
(Continued)

*Primary Examiner* — Robert W Morgan
*Assistant Examiner* — Chance L Smith
(74) *Attorney, Agent, or Firm* — Edell, Shapiro & Finnan, LLC

(57) ABSTRACT

Computer based methods, systems, and computer readable media for providing genomic services are provided. A request is received from a user. The request is applied to one or more from a group of a personalized data repository for the user and supporting knowledge bases, wherein the personalized data repository includes genetic test results, health/clinical information, and insurance coverage, and wherein the knowledge bases include information pertaining to genetic tests and clinical guidelines. Data from the applied request is integrated with results from service modules performing one or more from a group of content search, variation interpretation, and report generation to produce results for the request. The personalized data repository and supporting knowledge bases are updated based on the results of the request. Surveillance services are triggered based on one or more events.

20 Claims, 7 Drawing Sheets

(51) Int. Cl.
*G16H 10/20* (2018.01)
*G06F 40/279* (2020.01)
*G06N 20/00* (2019.01)

(56) References Cited

U.S. PATENT DOCUMENTS

| | | | | |
|---|---|---|---|---|
| 2004/0098204 | A1* | 5/2004 | Milosavljevic | G16H 70/20 |
| | | | | 702/20 |
| 2006/0136143 | A1* | 6/2006 | Avinash | G06Q 50/24 |
| | | | | 702/20 |
| 2008/0004848 | A1 | 1/2008 | Avey | |
| 2008/0131887 | A1 | 6/2008 | Stephan et al. | |
| 2009/0198519 | A1 | 8/2009 | McNamar | |
| 2010/0042438 | A1 | 2/2010 | Moore et al. | |
| 2010/0070455 | A1 | 3/2010 | Halperin et al. | |
| 2010/0094562 | A1* | 4/2010 | Shohat | G16B 20/00 |
| | | | | 702/19 |
| 2012/0116795 | A1* | 5/2012 | Ledley | G06Q 50/24 |
| | | | | 705/2 |
| 2015/0324527 | A1* | 11/2015 | Siegel | G16B 50/00 |
| | | | | 705/3 |
| 2017/0124263 | A1* | 5/2017 | Crafts, Jr. | G16H 70/20 |

OTHER PUBLICATIONS

Trakadis, Y.J. "Patient-controlled encrypted genomic data: an approach to advance clinical genomics." BMC Med Genomics 5, 31 (Jul. 20, 2012). (Year: 2012).*

Zhu, Qian et al. "Genetic testing knowledge base (GTKB) towards individualized genetic test recommendation—An experimental study," 2014 IEEE International Conference on Bioinformatics and Biomedicine (BIBM), Belfast, 2014, pp. 574-577. (Year: 2014).*

Blueprint Genetics. "Pricing" Aug. 16, 2014. (https://web.archive.org/web/20140816080311/http://blueprintgenetics.com/pricing/) (Year: 2014).*

Abugessaisa, Imad, et al. "Implementation of the CDC translational informatics platform-from genetic variants to the national Swedish Rheumatology Quality Register." Journal of translational medicine 11.1 (2013): 1-17. (Year: 2013).*

OncoGeneDx Custom Panel, https://www.genedx.com/test-catalog/available-tests/oncogenedx-custom-panel/, GeneDx, 2018, 3 pages.

Genomics Agilent, SureSelect Panels, https://www.genomics.agilent.com/en/SureSelect-DNA-Target-Enrichment-Baits-/SureSelect-Panels/?cid=AG-PT-124&tabId=AG-PR-1306&Nty=1&Ntx=mode+matchall&Ntk=BasicSearch&N=4294967292+4294967234+4294967294&type=baseSearch&No=0&Ntt=5190-4651, Agilent, retrieved from internet Jan. 2019, 3 pages.

Genetic Testing for Hereditary Cancer, Ambry Genetics, https://www.ambrygen.com/, retrieved from internet Jan. 2019, 3 pages.

Color, Color Population Health, https://pophealth.color.com, Color Genomics, Inc., 2019, 9 pages.

Philips genomics platform and Philips oncology platform, https://www.usa.philips.com/healthcare/medical-specialties/genomics/platform, retrieved from internet Jan. 2019, 5 pages.

"GTR: Genetic Testing Registry", NCBI, https://www.ncbi.nlm.nih.gov/gtr/, retrieved from internet Jan. 2019, 2 pages.

Castellanos et al., "A comprehensive custom panel design for routine hereditary cancer testing: preserving control, improving diagnostics and revealing a complex variation landscape." Scientific Reports, vol. 7, Article No. 39348 (2017), https://www.nature.com/articles/srep39348, Jan. 4, 2017, 12 pages.

Shaer et al., "GenomiX: A Novel Interaction Tool for Self-Exploration of Personal Genomic Data." In Proceedings of the 2016 CHI Conference on Human Factors in Computing Systems (CHI '16). ACM, New York, NY, USA, May 2016, pp. 661-672.

"Personalized Genetic Reports", https://www.23andme.com/dna-reports-list/, retrieved from internet Mar. 8, 2019, 6 pages.

* cited by examiner

PERSON-CENTRIC GENOMIC SERVICES FRAMEWORK AND INTEGRATED GENOMICS PLATFORM AND SYSTEMS

1. TECHNICAL FIELD

Present invention embodiments relate to genomic services and platforms, and more specifically, to person-centric platforms that provide information pertaining to a specific end-user and to integrated genomics platforms that identify trends in medical data.

2. DISCUSSION OF THE RELATED ART

Next-generation sequencing (NGS) for cancer testing is the standard of care for many clinical laboratories. The information provided from gene panel testing may impact multiple stages of clinical management including diagnostic classification, therapeutic intervention, treatment monitoring, and prognostic insights for a particular tumor. Commercially available gene panels are often pre-fabricated, having a fixed gene composition. As such, fabricated gene panel design services often lack flexibility due to a limited range of candidate genes and may be constrained by specific sequencing and variant detection methods utilized by a commercial sequencing lab.

Other constraints impacting gene panel testing involve financial, medical and clinical guidelines that are not fully incorporated into the workflow for gene panel selection. For example, although a genetic testing registry (GTR) platform may provide a central location for genetic test selection and comparison, this type of platform is typically not user-centric, and instead, may track commercial or population based factors such as genetic test type, associated phenotype, genetic mutations, and laboratory facilities. Additionally, the information submitted to the GTR platform usually is not independently verified and may contain errors or be incomplete.

Although genetic screening companies offer direct to consumer genetic tests that allow end consumers to assess their genetic predisposition for diseases, such services often require specific sample types, cover limited mutation types, and may only report genetic results for gene-trait/disease associations selected by individual companies rather than for a custom gene panel. For example, a consumer-based genetic testing service for genetic predisposition simply provides partial single nucleotide polymorphism (SNP) genotyping on saliva samples, associated with a limited number of diseases and inherited conditions.

SUMMARY

According to embodiments of the present invention, methods, systems and computer readable media for genomic services and a genomic platform are provided. A request is received from a user. The request is applied to one or more from a group of a personalized data repository for the user and supporting knowledge bases, wherein the personalized data repository includes genetic test results, health/clinical information, and insurance coverage, and wherein the knowledge bases include information pertaining to genetic tests and clinical guidelines. Data from the applied request is integrated with results from service modules performing one or more from a group of content search, variation interpretation, and report generation to produce results for the request. The personalized data repository and supporting knowledge bases are updated based on the results of the request. Surveillance services are triggered based on one or more events.

It is to be understood that the Summary is not intended to identify key or essential features of embodiments of the present disclosure, nor is it intended to be used to limit the scope of the present disclosure. Other features of the present disclosure will become easily comprehensible through the description below.

BRIEF DESCRIPTION OF THE DRAWINGS

Generally, like reference numerals in the various figures are utilized to designate like components.

DETAILED DESCRIPTION

Present techniques may provide person-centric information, usually based on genetic results that provide comprehensiveness and specificity for healthcare and clinical management for a specific end-user. Although pan-cancer gene panels (e.g., multigene panels with precisely targeted genes that are often commercially available, etc.), whole exome sequencing (WES), and whole genome sequencing (WGS) are routinely used in clinical settings to detect mutations in DNA/RNA derived from patient tumor samples, these techniques may be limited for small biological sample sizes. For example, when the quantity and/or quality of the tumor-derived DNA/RNA is small, having insufficient amounts of nucleic acids may complicate cancer genetic testing, especially when nucleic acids are obtained using techniques that produce a limited quantity of biomaterial (e.g., liquid biopsies, formalin fixed paraffin embedded (FFPE) tissue samples, etc.). In such cases, when a limited quantity of nucleic acids is available, or when rare variants need be identified with a high degree of confidence, small personalized targeted gene panels may be used to precisely identify genetic mutations in order to optimize therapeutic treatment.

Present techniques provide systems, services and platforms to customize personalized targeted gene panels for individual end-users. These personalized targeted gene panels have a variety of benefits including a relatively short turnaround time for obtaining results, timely incorporation of genetic test results with clinical management tools for treating cancer, as well as improved quality assurance from coupling personalized targeted gene panels with next generation sequencing (NGS) data. Present techniques may determine personalized targeted gene panels based on integrated inputs from different sources of information in a knowledge repository and based on end-user specific data, and may monitor new or changing information as a function of time to monitor end-user health longitudinally. Additionally, the platform may be used to uncover hidden factors that contribute to the development of diseases such as cancer.

Figure 1:
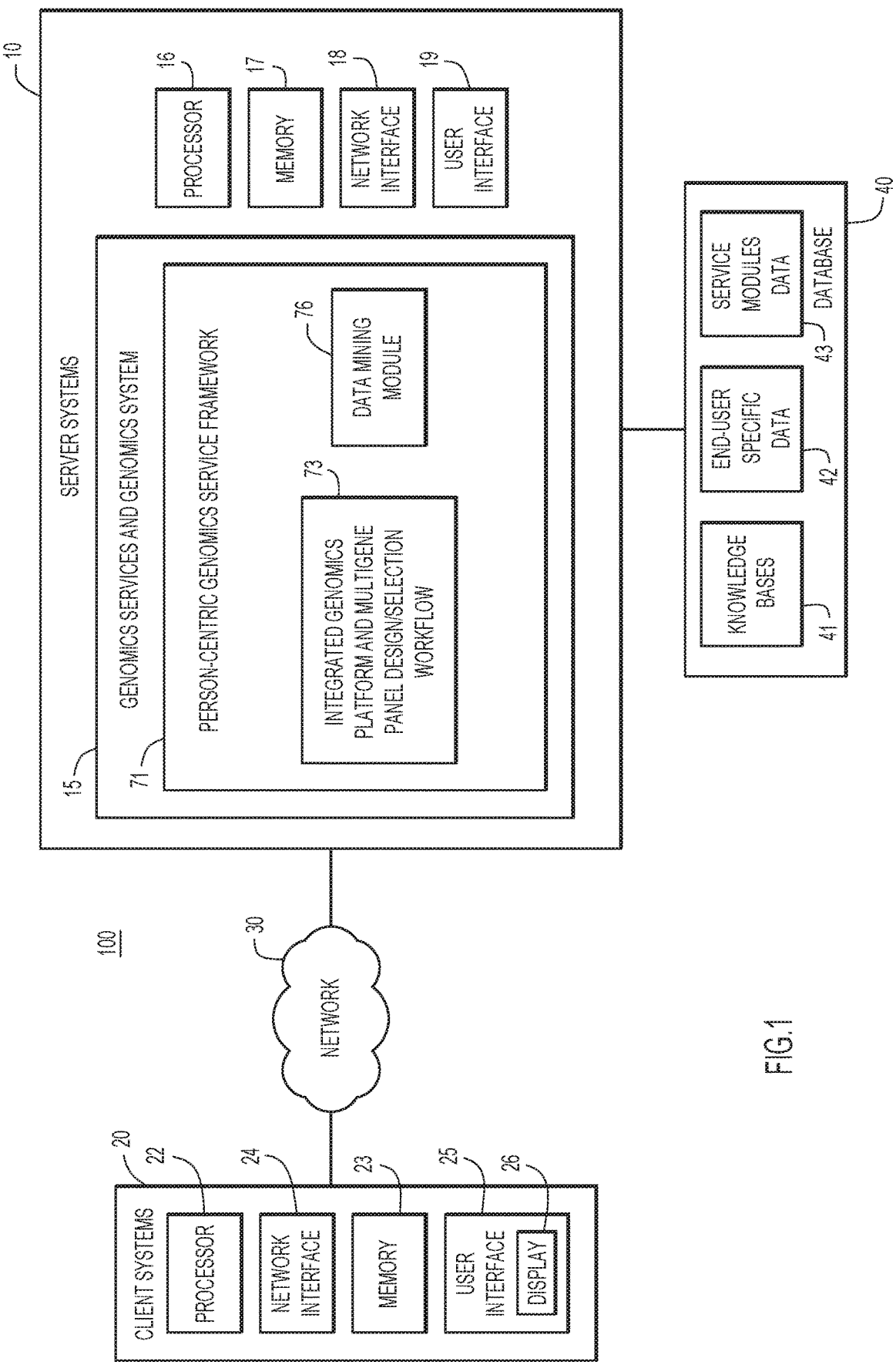
FIG. 1 is a block diagram of an example computing environment for the genomics services and genomics system, according to embodiments of the present disclosure.

An example environment 100 for use with present invention embodiments is illustrated in FIG. 1. Specifically, the environment includes one or more server systems 10 and one or more client or end-user systems 20. Server systems 10 and client systems 20 may be remote from each other and may communicate over a network 30. The network may be implemented by any number of any suitable communications media (e.g., wide area network (WAN), local area network (LAN), Internet, Intranet, etc.). Alternatively, server systems 10 and client systems 20 may be local to each other, and may communicate via any appropriate local communication medium (e.g., local area network (LAN), hardwire, wireless link, Intranet, etc.).

Client systems 20 enable users to access documents, services and other information (e.g., end-user specific information, omics information, longitudinal health information, medical information, financial information, knowledge bases, commercial gene panels, sequencing information, clinical guidelines, insurance information, biomedical literature and case data, data mining services, machine learning services, data search services, data interpretation services, report generation services, etc.) from server systems 10 and database 40 for analysis and review. Client systems 20 may provide access to the person-centric genomics service and genomics system 15 for at-risk end consumers, including cancer patients and genetic counselors representing patients, in order to provide information including gene testing, insurance guidelines, health information, information from knowledge bases and other information pertaining to germline mutations for hereditary cancer risk and/or somatic mutations. In some cases, a client may submit information (e.g., end-user specific medical records, genetic/omics test results, insurance information, etc.) for the analysis.

A database system 40 may store various information for the analysis (e.g., knowledge bases 41, end-user specific data 42, service modules data 43, etc.). The database system may be implemented by any conventional or other database or storage unit, may be local to or remote from server systems 10 and client systems 20, and may communicate via any appropriate communication medium (e.g., local area network (LAN), wide area network (WAN), Internet, hardwire, wireless link, Intranet, etc.). The client systems may present a graphical user (e.g., GUI, etc.) or other interface (e.g., command line prompts, menu screens, etc.) to solicit information from users pertaining to the desired documents and analysis, and may provide reports including analysis results (e.g., custom gene panel testing recommendations and guidelines, gene panels covered by an end-user's insurance, biomedical literature pertaining to new types of gene testing, results from mining a population of end-users relative to specific factors, results pertaining to longitudinal surveillance, etc.).

Server systems 10 and client systems 20 may be implemented by any conventional or other computer systems preferably equipped with a display or monitor 26, a base (e.g., including at least one processor 16, 22 one or more memories 17, 23 and/or internal or external network interfaces or communications devices 18, 24 (e.g., modem, network cards, etc.)), optional input devices (e.g., a keyboard, mouse or other input device) and/or user interface 19, 25 and any commercially available and custom software (e.g., person-centric genomics service framework software 71, software for service modules, server/communications software, browser/interface software, etc.).

Alternatively, one or more client systems 20 may provide a genomics services and genomics system when operating as a stand-alone unit. In a stand-alone mode of operation, the client system stores or has access to knowledge bases 41, end-user specific data 42, and an end-user centric genomics service framework including service modules and data generated by service modules. The graphical user (e.g., GUI, etc.) or other user interface (e.g., command line prompts, menu screens, etc.) may solicit information from a corresponding user pertaining to the analysis, and may provide reports including analysis results (e.g., custom gene panel testing recommendations and guidelines, gene panels covered by an end-user's insurance, biomedical literature pertaining to new types of gene testing, results from mining a population of end-users relative to specific factors, results pertaining to longitudinal surveillance, etc.).

Knowledge bases 41 may include information from databases and/or literature including commercially available gene panels 901, sequencing data 902, clinical guidelines for medical treatment 903, insurance guidelines 904, biomedical literature 905, and lung cancer explorer (LCE) case data 906. For example, commercially available gene panels 901 may include commercially available gene panels to identify genes and gene variants associated with diseases. Sequencing data 902 may identify mutations linked to diseases. Clinical guidelines 903 may contain information for treating particular diseases associated with particular mutations with specific drugs or drug combinations. Insurance guidelines 904 may contain information pertaining to therapeutics covered by insurance plans. Biomedical literature 905 may contain information pertaining to genes, gene variants, expressed proteins, transcripts, or other relevant molecules as well as biological pathways, drug targets, genes/gene variants associated with diseases, RNA translation levels associated with diseases, protein expression levels associated with diseases, etc. LCE case data 906 may contain lung cancer information derived from patient studies pertaining to genetic causes of lung cancer (e.g., including tumor tissue, non-malignant tissue (control), differential gene expression, expression-survival association, etc.). Knowledge bases may include data corresponding to a population of end-users (including patients) or may contain individual data (e.g., a literature case study for an end-user).

Literature documents and information from databases are presumed to be readable by a machine reader. In some aspects, optical character recognition may be used to recognize text in a document, to render the text readable and searchable. Additionally, text in tables, images, image captions, or lists may also be rendered machine readable. This processing ensures that images of documents, e.g., scanned PDFs, are included in the analysis. In some aspects, additional databases may be included in the knowledge base, specific to other types of cancer such as breast, pancreatic, ovarian, prostate, colon, liver, etc.

End-user specific medical data 42 may include specific information pertaining to the end-user including person-centric genomic information, health or medical information pertaining to the end-user, health insurance policies covering the end-user, etc. End-user specific data 42 may also include omics data (e.g., genomic, transcriptomic, proteomic, metabolomic, overexpression or underexpresssion of proteins, differential expression, etc.) specific to the end-user. Medical information may include an end-user's medical history (e.g., drug allergies, age, medical conditions, current medications, family history, genetic history, etc.). End-users may include healthy end-users as well as patients seeking treatment for or being treated for a disease or condition. For example, a healthy person with a family history of hereditary diseases may use this platform for gene screening and surveillance.

Figure 2:
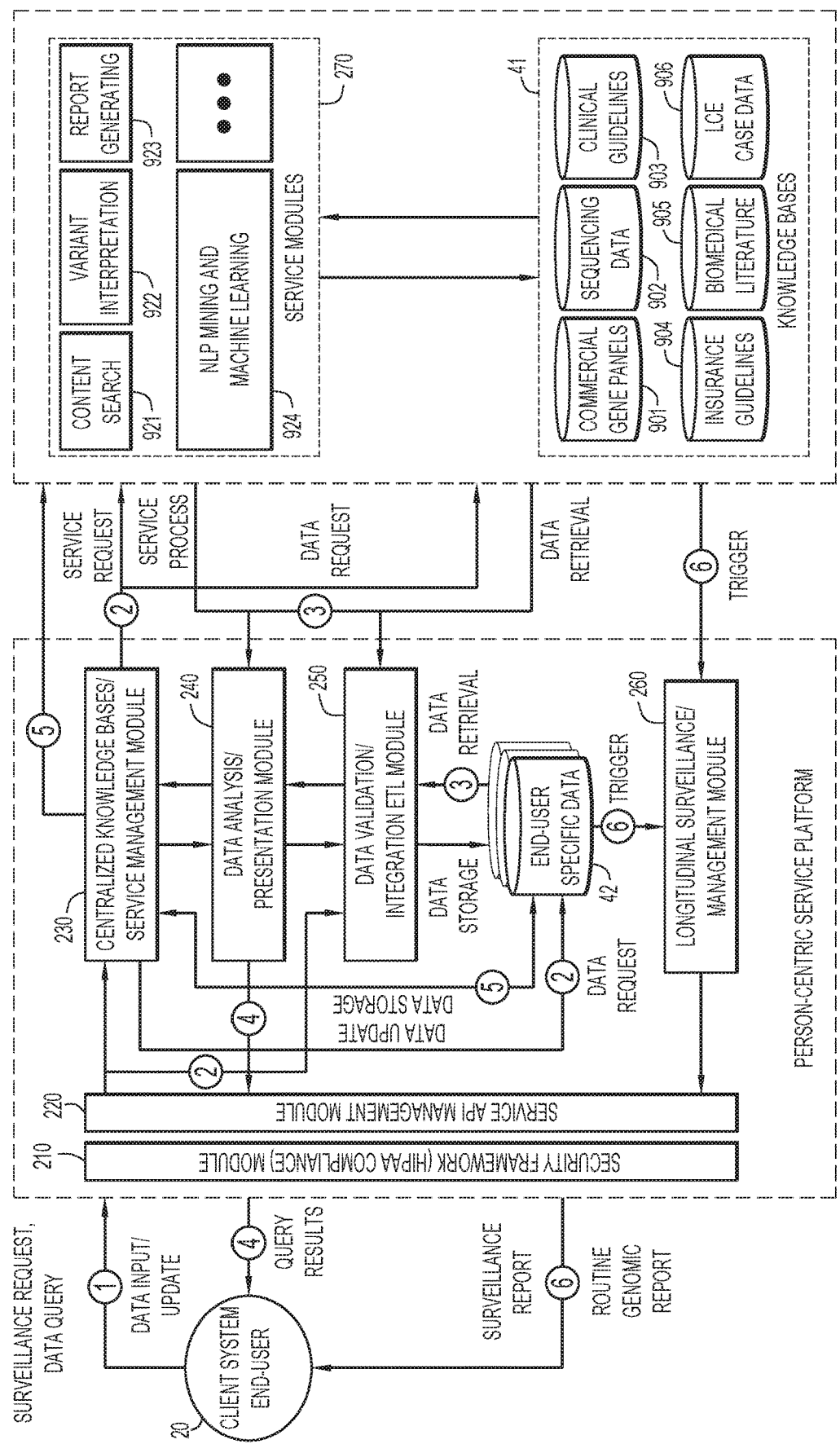
FIG. 2 is an example flowchart of a person-centric genomics service framework, according to embodiments of the present disclosure.

Person-centric genomics service framework 71 may provide individualized genomic services and longitudinal genomic/health surveillance and management services to an end-user. This framework provides a high degree of granularity and specificity to a particular end-user, including personalized gene panel design and selection as well as personalized genetic education and counseling through integrating data from end-user specific data 42, supporting knowledge bases 41, and supporting service modules 270 (as shown in FIG. 2) as well as corresponding service modules data 43. Service modules data 43 includes data generated by service modules 270 (e.g., the data produced by the services). Person-centric genomics service framework 71 may also enforce HIPAA compliance and provide data privacy/security, while providing personal longitudinal heath surveillance and management services to an end-user which may be triggered by various types of events and status changes (e.g., change in health status of an end-user, change in medical treatment of a patient, discovery of new gene variant/gene, discovery of new social or environmental factor for causing cancer, approval of new therapeutic, start of new clinical trial, etc.).

An integrated genomics platform and multigene panel design/selection workflow 73 may be deployed in service framework 71 to provide personalized gene panel design options and support improved decision making for gene panel selection for a particular end-user. The integrated multigene panel design/selection workflow may integrate inputs and services from different resources (see, FIGS. 2 and 3) to support improved decision making by end clients.

Data mining module 76 may be used to mine knowledge bases to identify hidden trends in data. For example, a user may provide a query to service framework 71, wherein the query contains an environmental factor, a social factor, a genetic factor, etc. The query may trigger analysis by the data mining module 76 to determine whether the factor correlates with an increase or decrease in the occurrence of a disease such as cancer for a patient population.

FIG. 2 shows a person-centric (individualized) genomics service framework 71, which may fulfill service requests such as design and selection of a personalized gene panel, provide data query services, and provide personal longitudinal health surveillance and management services as well as data mining services.

Components of the person-centric genomics service framework 71 may include security framework (Health Insurance Portability and Accountability Act (HIPAA) compliance) 210, service application programming interface (API) management layer 220, centralized knowledge bases/service modules management module 230, data analysis/presentation module 240, data validation/integration ETL module 250, longitudinal health surveillance and management module 260 as well as end-user specific data 42, knowledge bases 41, and service modules 270.

Service modules 270 may include a content search service 921, a variant interpretation service 922, a report generating service 923, an NLP mining and machine learning service 924, etc. Content search service 921 may search knowledge bases 41 and end-user specific data 42 for terms provided in the data query. Variant interpretation service 922 may evaluate variants from an end-user to determine whether the variant is likely to be a normal genetic variation in an end-user or is a variant causative of a disease.

NLP mining and machine learning service 924 may be trained to extract data from knowledge bases 41 and end-user specific data 42 using any combination of natural language processing (NLP) and machine learning techniques. For example, NLP mining and machine learning service 924 may use NLP and machine learning techniques to identify and extract information from the knowledge bases. The extracted information may be consolidated by the NLP mining and machine learning service. Report generating service 923 may be used to generate summaries of the extracted information. Report generating service 923 may also be used to provide reports of integrated information generated by data validation/integration ETL module 250, wherein the reports are provided to end-users of client systems 20. Types of information targeted for extraction may include health status information, genomic information, available treatments for diseases, etc.

Machine learning service 924 may use any suitable machine learning technique, including but not limited to statistical classification, supervised learning, unsupervised learning, artificial neural networks, deep learning neural networks, cluster analysis, random forest, dimensionality reduction, binary classification, decision tree, etc. to identify and extract various features, including but not limited to genomic information, end-user health status, rare mutations or genomic events, etc.

Security framework (HIPAA compliance) module 210 may provide de-identified data (e.g., from knowledge bases 41 and end-user specific data 42, including clinical and genomic data) to end-users. In some cases, end-users may be research institutes and/or companies in a consumer to business (C2B) model. The de-identified data may be evaluated for personally identifying information specific to an end-user, and this information may be removed or obscured within the data such that an individual cannot be identified from the data. Thus, the genomics services and genomics system 15 may act as an online vendor for distributing data while maintaining data privacy and security.

Service API management module 220 may receive communications from client systems 20 (e.g., including surveillance requests and data queries) and may provide results (e.g., query results, surveillance results, genomic or other reports, etc.) to the end-user. In some cases, healthcare providers or other healthcare partners may discuss with cancer patients or other end-users as to the types of queries to provide to the service framework or the types of longitudinal surveillance requests to provide to the service framework. In some cases, the longitudinal surveillance requests may include parameters or other settings for configuring longitudinal surveillance triggers that are managed by longitudinal surveillance and management module 250. Client systems 20 may also provide data inputs and data updates to the system to improve and update information stored in end-user specific data 42.

Centralized knowledge bases/service modules management layer 230 interfaces with the service modules 270 and knowledge bases 41 to provide service requests to these components of the system. When a surveillance request and/or data query is received, the centralized knowledge bases/service module management 230 sends the service request/query to service modules 270, and a data request to knowledge bases 41. Additionally, the data request is provided to end-user specific data database 42. Data returned from the query and/or service request is provided to data analysis/presentation module 240 and/or data validation/integration extract transform load (ETL) module 250. Centralized knowledge bases/service modules management module 230 may receive requests from client systems 20, via service API management module 220.

Data validation/integration ETL module 250 may receive results of the data query or surveillance request from service modules 270 and knowledge bases 41 as well as from end-user specific data 42. The validation/integration module may validate the received data to verify that the returned data is relevant to the data query and/or surveillance request. Additionally, the returned data from the knowledge bases and service modules may be integrated into the end-user specific data 42 using an extract transform load (ETL) process in which data is read and collected from the multiple databases of the knowledge bases, transformed into a form for storage into the destination database (e.g., end-user specific data 42), and loading the transformed data into the destination database. Once the data is validated, it may be provided to data analysis presentation module 240 for analysis and formatting for display to the end-user of client systems 20.

Data analysis/presentation module 240 may analyze data returned from data validation/integration ETL module 250, knowledge bases 41, and from service modules 270 and may format and send such data to client systems 20 for presentation to the end-user. Data analysis may include evaluating whether the data returned from service modules 270 and knowledge bases 41 is relevant to the query and to the specific end-user, in view of end-user specific information. In some aspects, the user may view the query results and may issue additional data queries or surveillance requests in response to the returned query results.

In general, many of the modules of the person-centric genomics framework may be in communication with each other. For example, the centralized knowledge bases/service management module 230 may communicate bidirectionally with data analysis/presentation module 240, and data analysis/presentation module 240 may communicate bidirectionally with data validation/integration ETL module 250. Data validation/integration ETL module 250 may communicate bidirectionally with patent specific data 42. The centralized knowledge bases/service management module 230 may also communicate bidirectionally with end-user specific data 42. Any of the service modules 270 may communicate bidirectionally with any of the knowledge bases 41. In some aspects, various services (e.g., content searching 921, variant interpretation 922, report generation 923, NLP mining and machine learning 924) may be used to identify and extract data from knowledge bases 41 (commercial gene panels 901, sequencing data 902, clinical guidelines 903, insurance guidelines 904, biomedical literature 905, LCE case data 906, etc.).

Longitudinal heath surveillance/management module 260 may receive requests for setting up longitudinal surveillance triggers. For example, a request may be received containing information to set up various service triggers including follow-up or routine genetic testing (e.g., based on a date), and once the date is reached, generation of a surveillance report is triggered. In other aspects, updates to the knowledge base (e.g., updates regarding gene function, gene/cancer relationships, clinical guidelines, etc.) may trigger generation of a surveillance report. In yet other aspects, new client surveillance requests or changes in personal health status may be received, which may trigger generation of a surveillance report. Longitudinal surveillance management module 260 may be configured to trigger generation of a surveillance report immediately upon receiving new information or upon detecting a change in the knowledge base. In other cases, the longitudinal surveillance management module 260 may be configured to generate reports on a daily, weekly, or monthly basis, depending upon the medical state of the end-user. The report may include end-user recommendation(s) based on the end user's medical status. The reporting interval may be customized based on the end-user's preference. For patients with aggressive forms of cancer, the system may be configured to run daily or weekly reports. For patients or healthy end-users who are at risk of cancer, for example, due to a genetic mutation, the system may be configured to run monthly, quarterly, or yearly reports.

End-user specific data 42 may contain end-user specific information for a plurality of individual end-users. For example, data for a particular end-user may be stored in end-user specific data 42 with a unique reference identifier, wherein the data may include genomic or medical history information for the end-user as well as information pertaining to medical insurance coverage for the end-user or any other factor described herein. This information may be used to select optimal gene panels for testing the end-user, to identify a particular disease such as cancer while also minimizing the costs associated with design of custom gene panels and optimizing testing for limited amounts of biological samples.

Changes in the information stored in end-user specific data 42, for a particular end-user may trigger execution of longitudinal surveillance report for that end-user. Changes in information stored in knowledge bases 41 may trigger execution of longitudinal surveillance reports for multiple end-users. The change may be evaluated for relevance to particular end-users, and if relevance is confirmed, an updated report (e.g., new gene panel testing, new treatments, new type of diagnosis, etc.) may be sent to each end-user, ensuring that the end-user has the most up-to-date information. The surveillance report may be sent through the API management service module 220 and security framework module 210, prior to presentation to the end-user. For example, if the report contains recommendations for a specific end-user and is provided to that same specific end-user, then de-identification is not needed. If the report is provided to a different end-user than to which the report is directed, then the system de-identifies the data prior to providing to the end-user, unless end-user authorization has been provided regarding release of the medical information.

Referring again to FIG. 2, a series of operations are shown for the modules of the person-centric genomics service framework. At operation 1, a surveillance request or data query from end consumers at the client system is received. Alternatively, new data or information from end consumers for data input or data update of end-user specific data is received. At operation 2, for a service-request or data-query, centralized knowledge bases/service management module 230 relays the service or data request to end-user specific data 42 and/or to the supporting knowledge bases and service modules. For data input or data updates, the data may be validated, integrated, and stored in end-user specific data 42. At operation 3, data obtained by supporting service modules operating on knowledge bases 41 may be provided to data validation/integration ETL module for processing. For example, the extracted data may be analyzed for completeness and validity. The processed data may be provided to data analysis/presentation module 240, for analysis and presentation to an end-user. At operation 4, query results or status results are returned to end consumers at client 20. At operation 5, query results or status results are provided to end-user specific data 42 to update personal data repositories and to knowledge bases to update supporting data repositories. At operation 6, longitudinal heath surveillance/management service may be triggered by multiple types of events including scheduled dates for follow-up or routine genetic testing, updates to the knowledge base (e.g., gene function, gene or cancer relationship, clinical guidelines, etc.), requests from end consumers or other health professionals, changes in personal health status, etc.

Longitudinal health monitoring may detect changes in an individual's health status. For example, if a new driver gene implicated in the development and progression of cancer is discovered, and the knowledge bases are updated, an end-user's omics information, stored in end-user specific data 42, may be evaluated for the presence of the driver gene. If the driver gene is detected, an end-user may be determined to have or be at high risk for a particular disease. The system may send a notice to the end user or to the physician or other end-user (if authorized by the end-user) regarding a status change of the end-user. As another example, if a new treatment becomes available (e.g., regulatory approval of a new therapeutic, availability of new types of treatment or diagnostic technology, initiation of new clinical trials, etc.), the physician or end-user may be notified regarding the availability of the new diagnostic test or treatment. In yet another example, the data in the respective knowledge bases may be integrated, such that a change in one type of database may be propagated through the other databases. For example, if NGS reveals a new tumor suppressor (e.g., from a frameshift mutation) then the system may evaluate end-user specific omics data to determine whether these end-users have the same mutation or a variant thereof. The system may design gene panels to detect the discovered mutation. Thus, longitudinal surveillance is not a passive process, but is based on a proactive dynamic framework.

Figure 3:
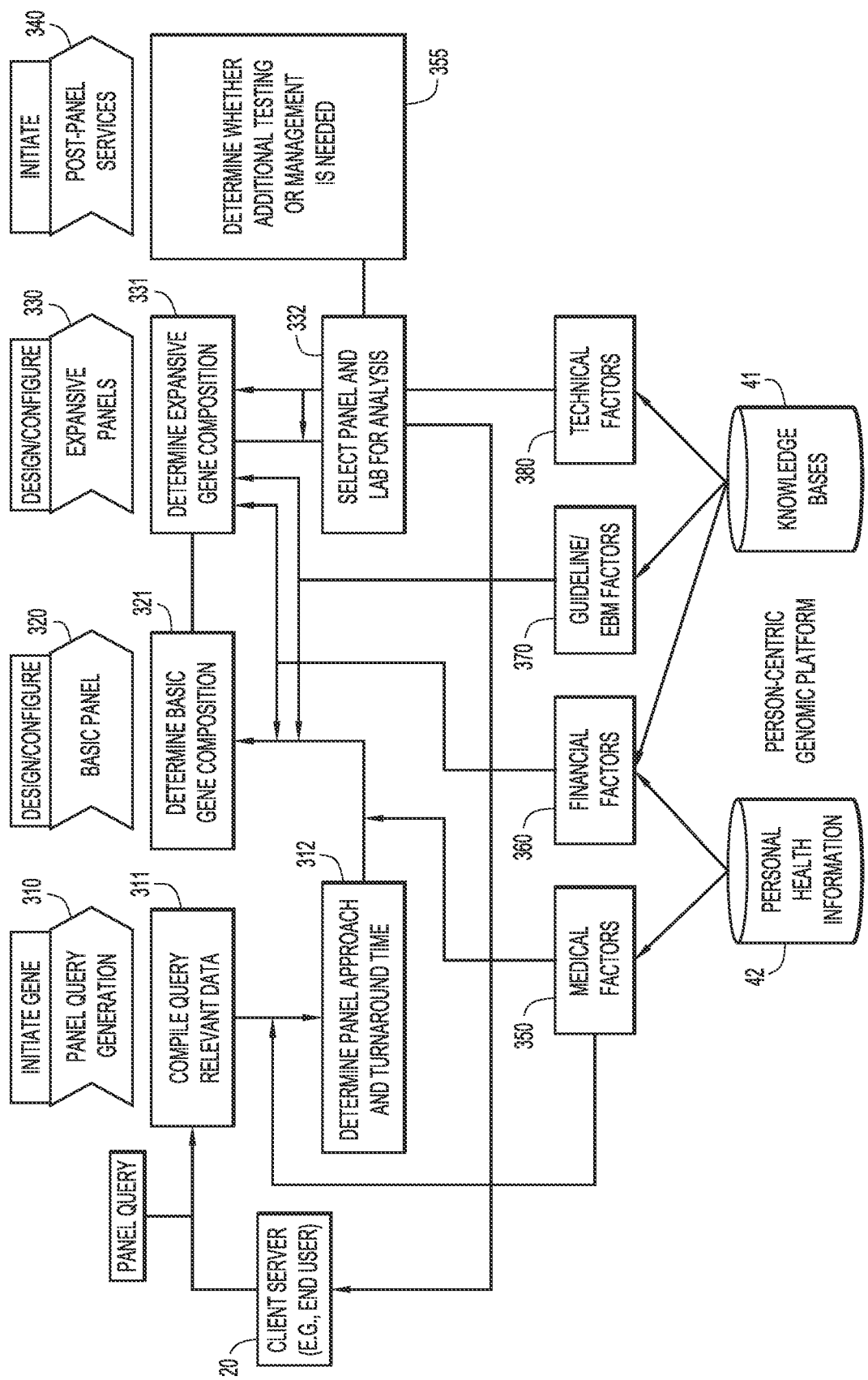
FIG. 3 is an example flowchart of designing a person-centric integrated multigene panel, according to embodiments of the present disclosure.

FIG. 3 shows an integrated multigene panel design/selection workflow that may be deployed in the framework of FIG. 2 to integrate inputs from various sources (e.g., medical factors, financial factors, guideline and evidence-based-medicine (EBM) factors and technical factors) for better personalized panel design and selection with corresponding NGS sequencing and analysis guidelines.

An end-user may initiate gene panel related services to customize a gene panel for a specific end-user. At operation 310, gene panel query generation is initiated. In particular, this may involve operations 311 and 312. At operation 311, relevant data to the query is compiled. A gene panel test purpose (e.g., screening for hereditary cancer, diagnosis of existing cancer, evaluation of cancer treatment) may be specified as well. At operation 312, query relevant data may be retrieved from end-user specific data 42 or supporting knowledge bases 41, and a panel approach and turnaround time may be determined. To determine a gene panel approach, the system may determine whether the gene panel should comprise cancer-specific markers (e.g., including markers not part of commercial gene panels or custom markers specific to an end-user) or pan-cancer markers (e.g., including markers available on commercially available gene panels to broadly screen for cancer). Additionally, various types of end-user information may be utilized, including personal health information, family information, biological sampling method (e.g., blood, tissue, FFPE, liquid biopsy, etc.). Additionally, tumor/normal pair information may be provided to the workflow. In other aspects, the gene panel may test for the presence of syndrome-specific markers. Once the type of gene panel has been determined (e.g., commercially available or custom), the amount of time needed to obtain results from the gene panel may be estimated. End-user related information may be stored in a medical factors database 350, and provided to other modules in the workflow. Medical factor database 350 may include age, gender, address, family history, family ethnicity, prior medical history (e.g., prior cancer diagnosis, prior cancer treatment, other diagnoses, etc.), and may be a subcomponent of end-user specific data 42.

At operation 320, a basic gene panel is designed for the specific end-user. In particular, at operation 321, the gene composition for a basic panel may be determined based on personal, medical, financial factors as well as clinical evidence/guidelines. In general, the basic gene panel may include genes with a high risk and penetrance (e.g., genes that occur with a high frequency in a population), established predictions (e.g., genes having a strong correlation with the presence of cancer), and available clinical management (e.g., genes with corresponding available therapeutic treatment). For this analysis, information from medical factors database 350 may be incorporated into the determination at operation 321, the information including cancer type, symptoms, age, gender, etc.

In some cases, it may be desirable to expand the basic customized gene panels for a specific end-user. The design of the gene panels may be expanded (to a multiple expansive gene panel) at operation 330 to include genes with moderate or low risk/penetrance, genes having evidence-based high risk but not yet recommended for testing by clinical guidelines, or newly identified relevant genes operation 331). In some cases, selection of specific genes for the multiple expansive gene panel operation 332) may be prioritized by financial, insurance, and other factors (e.g., coverage by end-user's insurance policy (e.g., covers a specific CPT code), cost, test frequency limit, coverage criteria, designated testing labs, etc.). In other cases, selection of specific genes for the multiple expansive gene panel (operation 332) may be prioritized by clinical guidelines or evidence-based medicine factors, such as NCCN guidelines, ClinVar guidelines, NGS sequencing guidelines, etc. Additionally, gene panel selection (operation 332) may be prioritized by local availability of commercial panels and sequencing labs, regional availability of commercial panels and sequencing labs, and other technical factors including NIH genetic testing registry sequencing methods and variant detection methods, etc. Gene panel and gene sequencing lab paired options may be provided to end users after prioritization by one or more of the aforementioned factors (e.g., local availability, regional availability, insurance coverage/policy, sequencing and detection methods, guidelines, etc.).

At operation 340, post-panel services are initiated. These services may include utilizing services and accessing information obtained by basic or expansive panels to improve gene panel selection during future workflows. After the gene panel is designed and results obtained, additional services at operation 355 may be requested. For example, the system may determine whether additional information or testing is needed. This may include NGS sequencing of end-user samples and variant interpretation/clinical management. In some cases, longitudinal query services may be configured to be triggered by arrival of genetic screening/testing results, updates in gene panels (expansion/modification), release of new guidelines, identifying new genes/variations, changes in personal health status, inputs from genetic/clinical professionals, etc. In some cases, NGS bioinformatics germline/ somatic analysis may be performed, variant interpretation may be conducted, and clinical management guidelines applied, etc.

Using this workflow, different gene panels, based on syndrome-specific genes, penetrance-specific genes, and/or cancer-specific genes, may be designed. Panels include commercially available and custom gene panels, which may be coupled with post-panel services. In some cases, commercial pan-cancer panels may be recommended, while in other cases, a customized personalized gene panel may be recommended by the genomics services and genomics system 15.

Medical factors 350 may include personal clinical and health information, family history and pedigree, cancer diagnosis/treatment, cancer type, symptoms, and age/gender, etc. Financial factors 360 may include insurance policy, CPT code, cost-coverage, etc. Guideline/evidence-based medicine (EBM) factors 370 may include National Comprehensive Cancer Network (NCCN) guidelines, ClinVar, NGS sequencing guidelines, etc. Technical factors 380 may include regional availability of gene panels/sequencing labs, variant detection, and interpretation methods, etc. In some cases, medical factors 350 and financial factors 360 may be included in end-user specific data 42. Guideline EBM factors 370 and technical factors 380 may be included in knowledge bases 41.

Post-panel services 340 may include analysis of emerging information in the cancer field. For example, recently identified, moderate/low penetrance genes may be identified in the literature as corresponding to particular types of cancer, and the omics data of the individual end-user may be evaluated to determine whether the individual has this gene. As another example, some gene variants of unknown significance (VUSs) may emerge as having an increased frequency as compared to other variants. The system 15 may globally evaluate all omics data of individuals to determine whether a correlation is observed with these variants and a particular type of cancer.

The integrated genomics platform may access and utilize any suitable omics information, including bisulfate sequencing type data, RNA sequencing data, mRNA data, diagnostic assay results, mass spectrometry analysis, immunohistocytochemistry (IHC) results, mutation analysis (e.g., frameshift, point, insertion, deletion, etc.), protein expression, microarray data, etc. This data may be integrated with medical factors 350, financial factors 360, clinical guidelines/EBN factors 370, as well as technical factors 380.

Figure 4A:
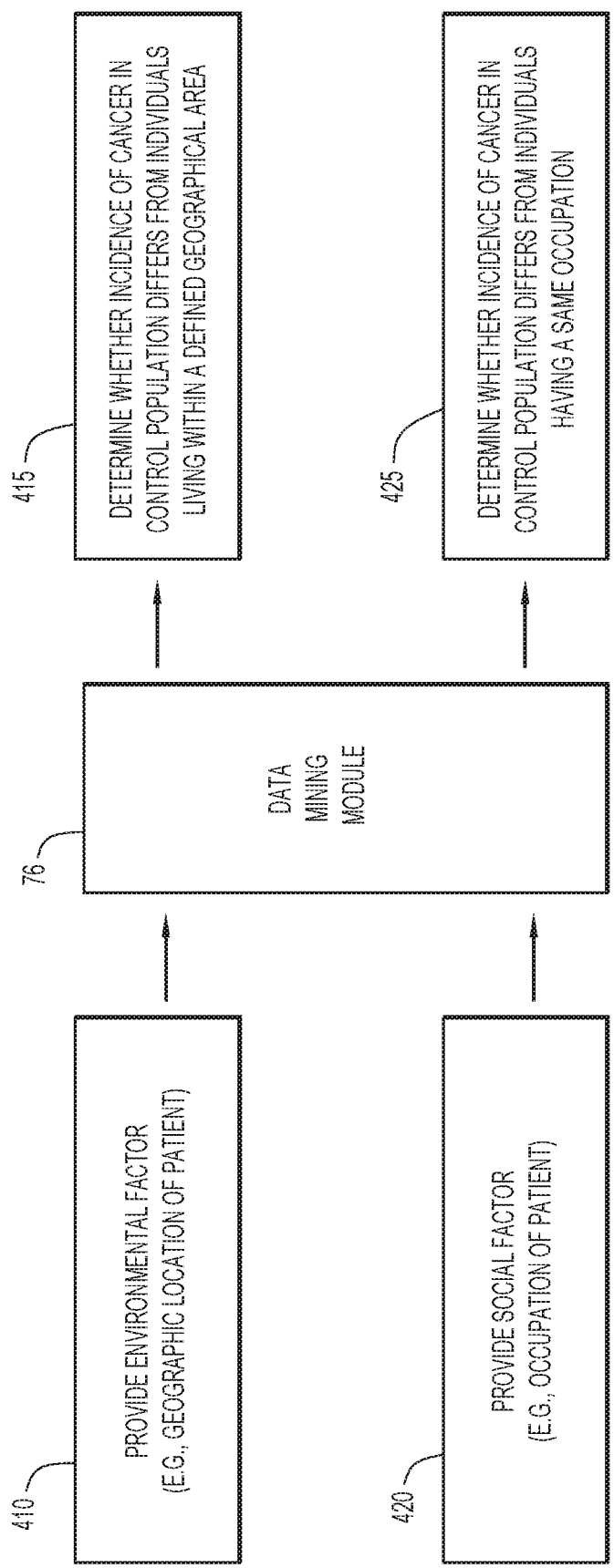
FIG. 4A is an example flowchart of using a data mining module to identify social and geographic factors that impact disease, according to embodiments of the present disclosure.
Figure 4B:
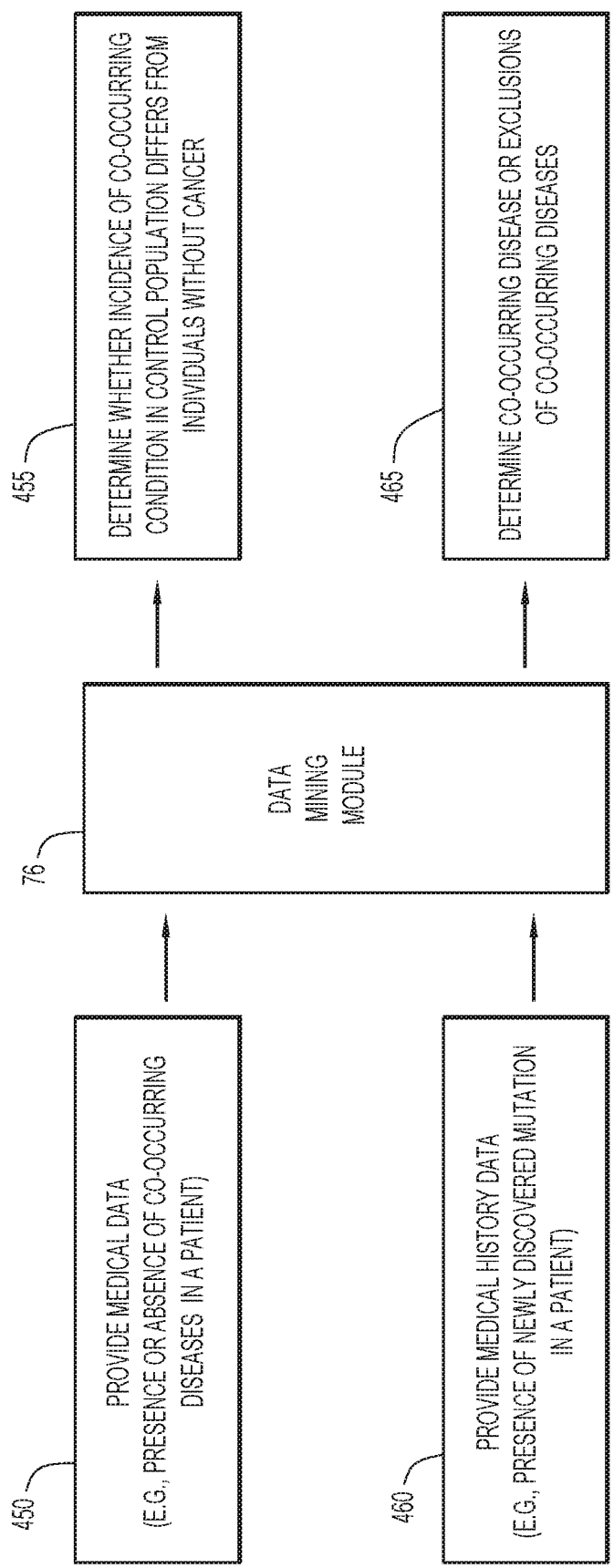
FIG. 4B is an example flowchart of using the data mining module to identify genetic factors that impact disease, according to embodiments of the present disclosure.

FIGS. 4A-4B show examples of mining data using data mining module 76 to determine hidden trends in data (e.g., genetic or environmental factors correlated with the presence of a disease). In some aspects, the data may be mined to detect trends (e.g., incidence of cancer in individuals having a newly discovered mutation). In other aspects, the data may be mined to detect environmental or social trends (e.g., correlation of a disease with a geographical area, correlation of a disease with an occupation, etc.) or genetic trends (e.g., a mutation among a population of individuals having a same disease, etc.). In still other aspects, the data may be evaluated with respect to co-occurring conditions (e.g., heart disease, cancer, etc.) to determine if the presence of one type of disease increases or decrease the likelihood of occurrence of the second type of disease. In some aspects, data mining may be offered as a service, with the ability to mine integrated data to determine hidden or obscure disease factors and relationships based upon custom queries generated by an end-user.

FIG. 4A shows an example of a data mining module uncovering hidden relationships between diseases and social or environmental factors encompassing a population of end-users. At operation 410, the data mining module 76 may be provided with population data including a geographic location for each end-user. The data may be analyzed with respect to a specific defined geographical area (e.g., a 1 mile radius, a 2 mile radius, etc.). At operation 415, by comparing a control population of individuals dispersed across a large geographical area to a targeted geographical area (e.g., a defined geographical area), the data mining module 76 may statistically determine whether individuals living within the defined geographical area have a higher incidence of cancer or other disease than individuals in a disperse geographical area.

As another example, at operation 420, the data mining module 76 may be provided with population data including an occupation of each end-user. At operation 425, by comparing a control population of individuals having diverse types of occupations to a specific population having a same occupation, the data mining module 76 may statistically determine whether individuals with a specific occupation have a higher incidence of cancer or other diseases than the general population. Any suitable environmental or social factor may be analyzed in this manner.

FIG. 4B shows an example of data mining module 76 uncovering hidden relationships between diseases and genetic factors. For example, at operation 450, the data mining module may be provided with medical data, including end-users with two or more diseases as well as the corresponding types of diseases. At operation 455, the data may be analyzed for co-occurrence of diseases or exclusions of combination of diseases. For example, a user may query the system to statistically determine if end-users having cardiac disease are less likely to have cancer (e.g., an exclusion or reduction in the occurrence of cancer and cardiac disease in an end-user), as compared to the general population. As another example, the system may be queried to statistically determine whether an end-user with a gastrointestinal stromal tumor is more likely to have hepatocellular carcinoma, as compared to the general population (e.g., a co-occurrence of two diseases in an end-user). Any suitable mutation or genetic factor may be analyzed in this manner.

As another example, at operation 460, the data mining module is provided medical history data including a newly discovered mutation identified in a population of end-users. At operation 465, the data may be analyzed with respect to the novel mutation to statistically determine whether a control population without the mutation has a lower or higher incidence of cancer than individuals with the mutation. Alternatively, the data mining module may be used to identify specific types of cancer associated with the mutation (e.g., individuals with breast cancer may have this mutation while individuals with colon cancer do not).

Thus, the system is able to analyze the end-user specific data 42 to uncover novel relationships, including relationships between various factors (e.g., between environmental, social, and genetic data), co-occurrences of factors, and exclusions of combinations of factors.

Figure 5:
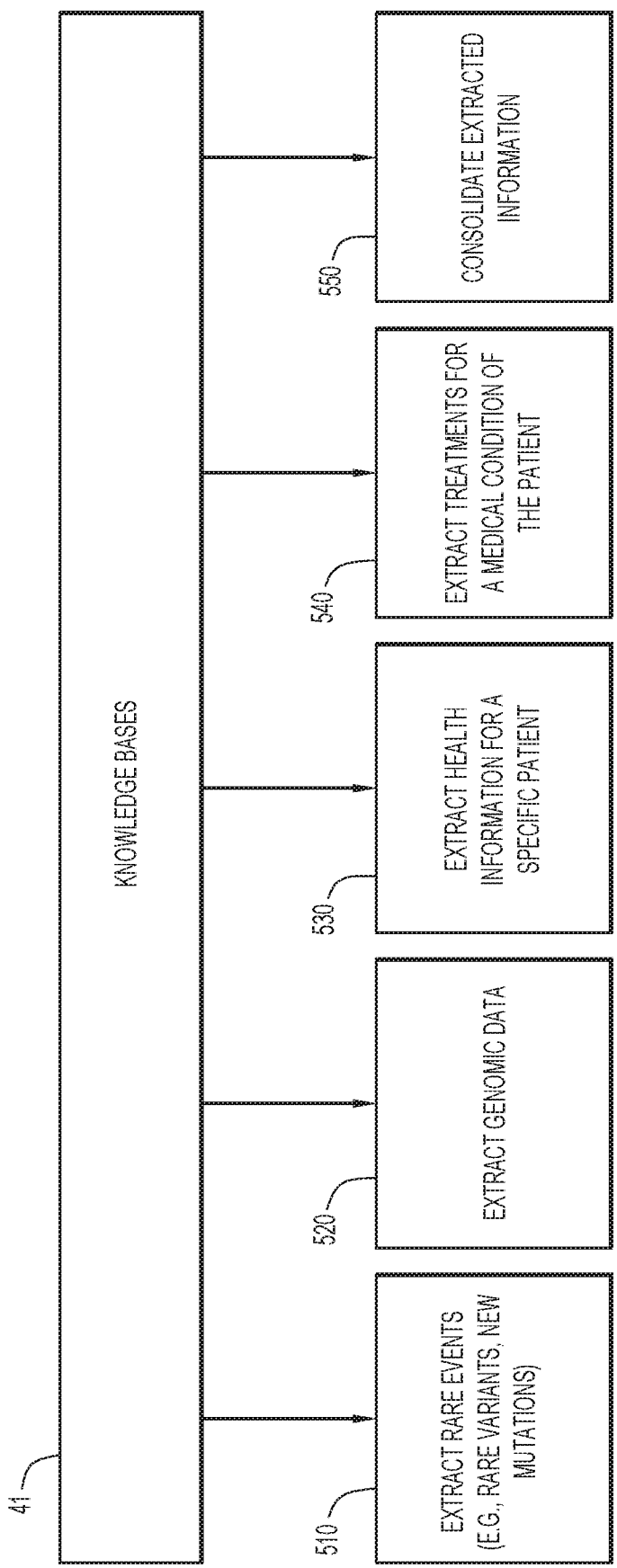
FIG. 5 shows examples of the types of information that may be extracted and/or consolidated by the machine learning module and/or natural language processing module, according to embodiments of the present disclosure.

FIG. 5 is an illustration of functions of the NLP mining and machine learning module 924 to the person-centric genomics service framework, to extract various types of information. This extracted information may be provided to data validation/integration ETL module 250 and/or data analysis/presentation module 240.

In some aspects, the data query may contain a request to obtain end-user specific information, for example, regarding a rare variant or newly identified mutation. At operation 510, the NLP mining and machine learning service module may be used to analyze and extract information from the corpus of knowledge bases to identify information pertaining to the new mutation or variant. Once identified, the service modules may extract related information pertaining to treatments (if known) for individuals having the new identified or rare mutation.

At operation 520, the NLP and machine learning service modules may extract genomic data corresponding to the rare or newly identified mutation. For example, omics information (e.g., genomic, transcriptomic and/or proteomic information pertaining to molecules that are overexpressed, underexpressed or otherwise altered in the present of the new or rare mutations, etc.) may be extracted, and used to identify biological pathways impacted by the mutation as well as possible treatments. Additionally, NLP and machine learning service modules may determine the likelihood that a variant is a mutation or normally occurring (e.g., not associated with a disease).

At operation 530, the NLP and machine learning service modules may extract information pertaining to a health status of an individual, for example, an individual having the new or rare mutation.

At operation 540, NLP and machine learning service modules may extract medical treatments for a medical condition of an end-user. For example, if new or rare mutations are discovered for a disease, the system may evaluate genomic information (if available) to determine if the mutations are present in the end-user. If the mutations are present in the end-user, the system may determine whether treatments are available (e.g., by targeting the biological pathway (if known) in which the mutation is found).

At operation 550, the NLP and machine learning service modules may consolidate extracted information. In some cases, the NLP and machine learning service modules may remove redundant information, and may format the extracted information as a summary.

Figure 6:
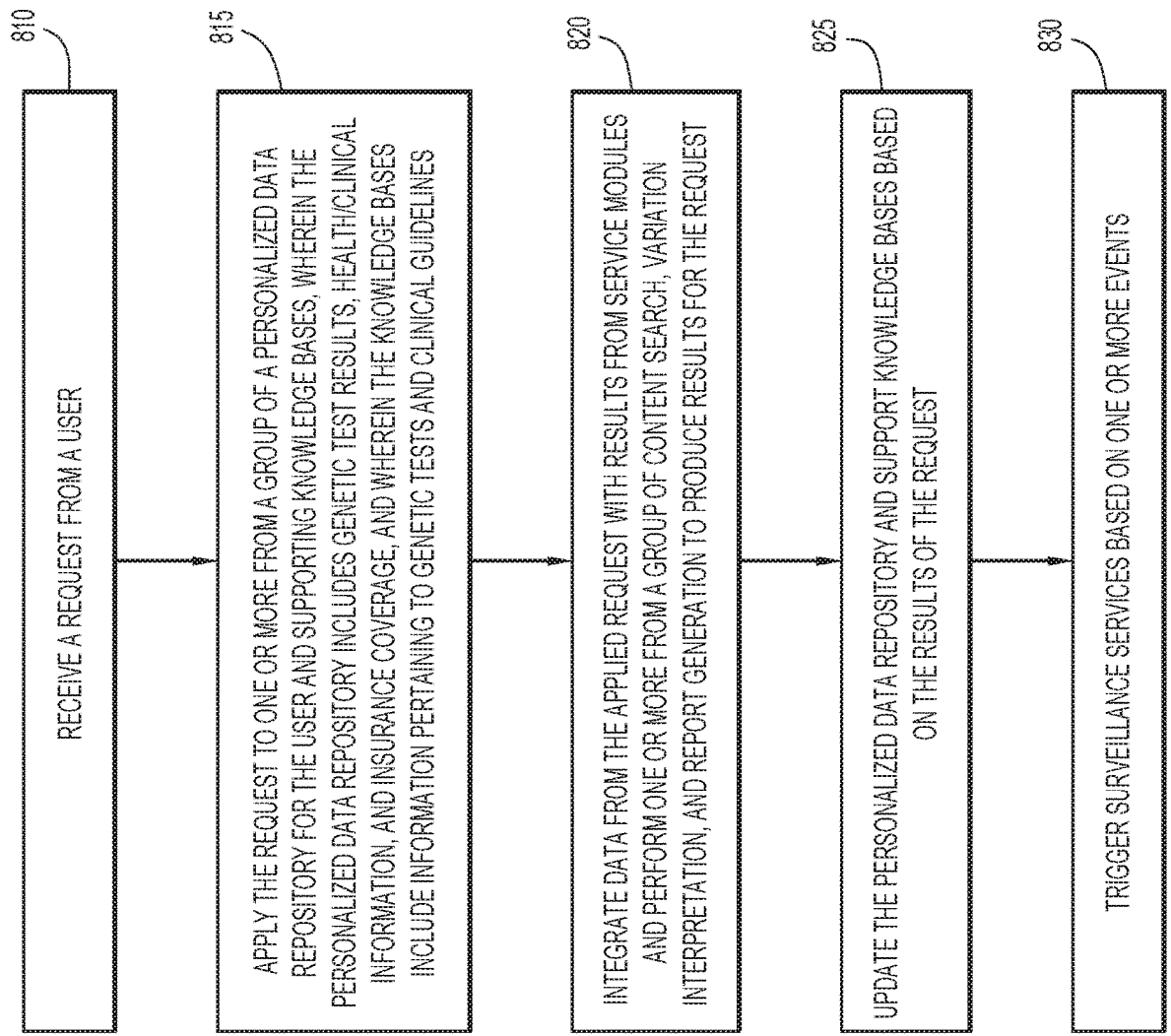
FIG. 6 is a high level flow diagram showing operations of the person-centric genomics services system, according to embodiments of the present disclosure.

FIG. 6 shows a high level flowchart of the operations of the genomics services and genomics system 15. At operation 810, a request is received from a user. At operation 815, the request is applied to one or more from a group of a personalized data repository for the user and supporting knowledge bases, wherein the personalized data repository includes genetic test results, health/clinical information, and insurance coverage, and wherein the knowledge bases include information pertaining to genetic tests and clinical guidelines. At operation 820, data from the applied request is integrated with results from service modules and one or more from a group of content search, variation interpretation, and report generation is performed to produce results for the request. At operation 825, the personalized data repository and support knowledge bases are updated using results of the request, which may involve end-user personal data. To perform the update, the system may need consent from the end-user and/or may perform de-identification of the end user's data. At operation 830, surveillance services are triggered based on one or more events.

Present techniques improve personal healthcare management. Individualization of gene panel design and selection can be tailored to a specific end-user to determine optimal testing strategies for the end-user. Additionally, small multigene panel testing enables the detection of rare mutations in blood/plasma, using techniques such as liquid biopsy, to guide clinical management and therapeutic strategies. For example, using this approach, newly acquired drug resistance mutations can be detected, cancer screening can be performed, and disease progression or treatment resistance can be detected. A person-centric genomics service framework may be used to access highly personalized genomics data and to manage routine genetic tests. Additionally, a person-centric service framework may offer individualized services with greater granularity and may provide personal longitudinal heath surveillance and management in a digital health environment.

Present techniques provide a person-centered (individualized) genomics service framework to fulfill end consumers' service requests such as personalized gene panel design/selection and data query, and to provide personal longitudinal heath surveillance and management services. Present techniques also provide a data repository for personal health and genomic profiles, containing data about personal routine genetic test results, health/clinical information, insurance coverage, etc., and access to various supporting knowledge-bases (e.g., including or related to commercially available gene panels/genetic tests provided by CLIA certified labs, clinical guidelines, insurance policy and coverage criteria from major insurance agencies, etc.) as well as access to various supporting service platforms (e.g., services of content search 921, variant interpretation 922, report generating 923, NLP mining and machine learning 924, etc.). Additionally, the data may be provided in a secure manner that is compliant with patient privacy and laws.

In other aspects, an integrated multigene panel design/selection workflow is provided in which services of custom gene panel design/selection and corresponding NGS sequencing/analysis guidelines are based on supporting data and knowledge integration. Post panel-selection services are provided such as genetic education/counseling (clinical utility of genetic tests, tiered and binned genetic counseling, variant interpretation, clinical management and risk-reduction measurements, etc.) and longitudinal services (routine genetic screening/testing advice, gene panel updating, etc.)

It will be appreciated that the embodiments described above and illustrated in the drawings represent only a few of the many ways of implementing embodiments for providing person-centric genomics services frameworks, workflows, and platforms.

The environment of the present invention embodiments may include any number of computer or other processing systems (e.g., client or end-user systems, server systems, etc.) and databases or other repositories arranged in any desired fashion, where the present invention embodiments may be applied to any desired type of computing environment (e.g., cloud computing, client-server, network computing, mainframe, stand-alone systems, etc.). The computer or other processing systems employed by the present invention embodiments may be implemented by any number of any personal or other type of computer or processing system (e.g., desktop, laptop, PDA, mobile devices, etc.), and may include any commercially available operating system and any combination of commercially available and custom software (e.g., browser software, communications software, server software, genomics services and genomics system 15, software for knowledge bases 41, software for service modules 270, etc.). These systems may include any types of monitors and input devices (e.g., keyboard, mouse, voice recognition, etc.) to enter and/or view information.

It is to be understood that the software (e.g., genomics services and genomics system 15, including person-centric genomics service framework 71, integrated genomics platform and multigene pane design/selection workflow 73, and data mining module 76, etc.) of the present invention embodiments may be implemented in any desired computer language and could be developed by one of ordinary skill in the computer arts based on the functional descriptions contained in the specification and flow charts illustrated in the drawings. Further, any references herein of software performing various functions generally refer to computer systems or processors performing those functions under software control. The computer systems of the present invention embodiments may alternatively be implemented by any type of hardware and/or other processing circuitry.

The various functions of the computer or other processing systems may be distributed in any manner among any number of software and/or hardware modules or units, processing or computer systems and/or circuitry, where the computer or processing systems may be disposed locally or remotely of each other and communicate via any suitable communications medium (e.g., LAN, WAN, Intranet, Internet, hardwire, modem connection, wireless, etc.). For example, the functions of the present invention embodiments may be distributed in any manner among the various end-user/client and server systems, and/or any other intermediary processing devices. The software and/or algorithms described above and illustrated in the flow charts may be modified in any manner that accomplishes the functions described herein. In addition, the functions in the flow charts or description may be performed in any order that accomplishes a desired operation.

The software of the present invention embodiments (e.g., genomics services and genomics system 15, including person-centric genomics service framework 71, integrated genomics platform and multigene panel design/selection workflow 73, and data mining module 76, etc.) may be available on a non-transitory computer useable medium (e.g., magnetic or optical mediums, magneto-optic mediums, floppy diskettes, CD-ROM, DVD, memory devices, etc.) of a stationary or portable program product apparatus or device for use with stand-alone systems or systems connected by a network or other communications medium.

The communication network may be implemented by any number of any type of communications network (e.g., LAN, WAN, Internet, Intranet, VPN, etc.). The computer or other processing systems of the present invention embodiments may include any conventional or other communications devices to communicate over the network via any conventional or other protocols. The computer or other processing systems may utilize any type of connection (e.g., wired, wireless, etc.) for access to the network. Local communication media may be implemented by any suitable communication media (e.g., local area network (LAN), hardwire, wireless link, Intranet, etc.).

The system may employ any number of any conventional or other databases, data stores or storage structures (e.g., files, databases, data structures, data or other repositories, etc.) to store information (e.g., knowledge bases 41, end-user specific data 42, service modules data 43, reports, etc.). The database system may be implemented by any number of any conventional or other databases, data stores or storage structures (e.g., files, databases, data structures, data or other repositories, etc.) to store information (e.g., knowledge bases 41, end-user specific data 42, service modules data 43, reports, etc.). The database system may be included within or coupled to the server and/or client systems. The database systems and/or storage structures may be remote from or local to the computer or other processing systems, and may store any desired data (e.g., knowledge bases 41, end-user specific data 42, service modules data 43, reports, etc.).

The present invention embodiments may employ any number of any type of user interface (e.g., Graphical User Interface (GUI), command-line, prompt, etc.) for obtaining or providing information (e.g., knowledge bases 41, end-user specific data 42, service modules data 43, reports, etc.), where the interface may include any information arranged in any fashion. The interface may include any number of any types of input or actuation mechanisms (e.g., buttons, icons, fields, boxes, links, etc.) disposed at any locations to enter/display information and initiate desired actions via any suitable input devices (e.g., mouse, keyboard, etc.). The interface screens may include any suitable actuators (e.g., links, tabs, etc.) to navigate between the screens in any fashion.

The report may include a listing of results along with any other information arranged in any fashion, and may be configurable based on rules or other criteria to provide desired information to a user (e.g., data requests, surveillance requests, etc.).

The present invention embodiments are not limited to the specific tasks or algorithms described above, but may be utilized for any application in which person-centric information is needed.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises", "comprising", "includes", "including", "has", "have", "having", "with" and the like, when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises a document of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A method of providing genomic services comprising:
receiving a request from a user, wherein the request pertains to a multigene panel selection;
retrieving information for the multigene panel selection from a personalized data repository for the user and supporting knowledge bases, wherein the retrieved information includes medical information of the user, wherein the retrieved information includes omics information comprising overexpression and underexpression of proteins, and wherein the retrieved information is identified and extracted using a service module configured to perform natural language processing and machine learning;

determining gene composition for the multigene panel selection based on the retrieved information, wherein gene composition is selected based on a risk of each gene, an established prediction of each gene, a financial cost for including each gene, a clinical guideline, and available clinical management for each gene;

applying the request to one or more from a group of the personalized data repository for the user and the supporting knowledge bases, wherein the personalized data repository includes genetic test results, health/clinical information, and insurance coverage, and wherein the knowledge bases include information pertaining to genetic tests and clinical guidelines;

integrating data from the applied request with results from service modules and performing one or more from a group of content search, variation interpretation, and report generation to produce results for the request;

updating the personalized data repository and supporting knowledge bases to include the results of the request and health status results of the user, wherein the personalized data repository is updated by integrating and validating the results of the request using an extract, transform, and load process, and wherein updating the personalized data repository and supporting knowledge bases improves gene panel selection during future workflows; and triggering surveillance services based on one or more events, wherein updating the personalized data repository and supporting knowledge bases triggers the surveillance services, wherein the surveillance services generate a surveillance report in response to the triggering, and wherein the surveillance services include longitudinal health monitoring to identify a change in a health status of the user.

2. The method of claim 1, wherein determining the gene composition for the multigene panel selection comprises determining gene composition for one of a basic panel and a multiple expansive panel; and the method further comprises:
performing services based on the determined panel including one or more from a group of: NGS sequencing and variant interpretation/clinical management, genetic screening/testing advice, gene panel updating, producing new guidelines, identifying new genes/variations, and identifying personal health status changes.

3. The method of claim 1, wherein the request comprises an environmental factor or a social factor, and the method further comprising:
applying the request to the personalized data repository, wherein the personalized data repository comprises the environmental factor or the social factor for each user of a population of users;
integrating data pertaining to the environmental factor or the social factor for each of the population of users from the applied request with the results from the service modules; and
analyzing the integrated data to determine whether the environmental factor or the social factor increases or decreases a prevalence of a disease in the population relative to a control population of users.

4. The method of claim 1, wherein the request comprises a genetic factor, and the method further comprising:
applying the request to the personalized data repository for a population of users and supporting knowledge bases, wherein the personalized data repository comprises the genetic factor for each user of a population of users;
integrating data pertaining to the genetic factor for each user of the population of users from the applied request with the results from the service modules; and
analyzing the integrated data to determine whether the genetic factor increases or decreases a prevalence of a disease in the population relative to a control population of users.

5. The method of claim 1, further comprising:
extracting, using the service module configured to perform natural language processing and machine learning, person-centric data pertaining to the applied request from the personalized data repository and from the supporting knowledge bases; and
consolidating the extracted data and including the consolidated data in the results for the request.

6. The method of claim 2, further comprising:
determining the gene composition for the multiple expansive panel based on one or more factors selected from the group consisting of medical factors, financial factors, clinical guideline factors, and technical factors.

7. The method of claim 1, further comprising:
sending a notification to a user including results of triggering the surveillance services.

8. The method of claim 1, wherein the events include a newly discovered gene, a change in an end-user's medical status, a change in a clinical guideline, or a change in the composition of a gene panel.

9. A system for providing genomic services, wherein the system comprises at least one processor configured to:
receive a request from a user, wherein the request pertains to a multigene panel selection;
retrieving information for the multigene panel selection from a personalized data repository for the user and supporting knowledge bases, wherein the retrieved information includes medical information of the user, wherein the retrieved information includes omics information comprising overexpression and underexpression of proteins, and wherein the retrieved information is identified and extracted using a service module configured to perform natural language processing and machine learning;
determining gene composition for the multigene panel selection based on the retrieved information, wherein gene composition is selected based on a risk of each gene, an established prediction of each gene, a financial cost for including each gene, a clinical guideline, and available clinical management for each gene;
apply the request to one or more from a group of the personalized data repository for the user and the supporting knowledge bases, wherein the personalized data repository includes genetic test results, health/clinical information, and insurance coverage, and wherein the knowledge bases include information pertaining to genetic tests and clinical guidelines;
integrate data from the applied request with results from service modules and perform one or more from a group of content search, variation interpretation, and report generation to produce results for the request;
update the personalized data repository and supporting knowledge bases to include the results of the request and health status results of the user, wherein the personalized data repository is updated by integrating and validating the results of the request using an extract, transform, and load process, and wherein updating the personalized data repository and supporting knowledge bases improves gene panel selection during future workflows; and trigger surveillance services based on one or more events, wherein updating the personalized data repository and supporting knowledge bases triggers the surveillance services, wherein the surveillance services generate a surveillance report in response to the triggering, and wherein the surveillance services include longitudinal health monitoring to identify a change in a health status of the user.

10. The system of claim 9, wherein determining the gene composition for the multigene panel selection comprises determine gene composition for one of a basic panel and a multiple expansive panel based on the retrieved information; and wherein the at least one processor is further configured to:

perform services based on the determined panel including one or more from a group of: NGS sequencing and variant interpretation/clinical management, genetic screening/testing advice, gene panel updating, producing new guidelines, identifying new genes/variations, and identifying personal health status changes.

11. The system of claim 9, wherein the request comprises an environmental factor or a social factor, and the at least one processor is further configured to:

apply the request to the personalized data repository, wherein the personalized data repository comprises the environmental factor or the social factor for each of a population of users;

integrate data pertaining to the environmental factor or the social factor for each of the population of users from the applied request with the results from the service modules; and analyze the integrated data to determine whether the environmental factor or the social factor increases or decreases a prevalence of a disease in the population relative to a control population of users.

12. The system of claim 9, wherein the request comprises a genetic factor, and the at least one processor is further configured to:

apply the request to the personalized data repository for a population of users and supporting knowledge bases, wherein the personalized data repository comprises the genetic factor for each of a population of individuals;

integrate data pertaining to the genetic factor for each of the population of individuals from the applied request with the results from the service modules; and analyze the integrated data to determine whether the genetic factor increases or decreases a prevalence of a disease in the population relative to a control population of individuals.

13. The system of claim 9, wherein the at least one processor is further configured to:

extract, using the service module configured to perform natural language processing and machine learning, person-centric data pertaining to the applied request from the personalized data repository and from the supporting knowledge bases; and consolidate the extracted data and include the consolidated data in the results for the request.

14. The system of claim 10, wherein the at least one processor is further configured to:

determine the gene composition for the multiple expansive panel based on one or more factors selected from the group consisting of medical factors, financial factors, clinical guideline factors, and technical factors.

15. The system of claim 9, wherein the at least one processor is further configured to:

send a notification to a user including results of triggering the surveillance services.

16. The system of claim 9, wherein the events include a newly discovered gene, a change in an end-user's medical status, a change in a clinical guideline, or a change in a composition of a gene panel.

17. A computer program product for providing genomic services, the computer program product comprising one or more computer readable storage media collectively having program instructions embodied therewith, the program instructions executable by a computer to cause the computer to:

receive a request from a user, wherein the request pertains to a multigene panel selection;

retrieving information for the multigene panel selection from a personalized data repository for the user and supporting knowledge bases, wherein the retrieved information includes medical information of the user, wherein the retrieved information includes omics information comprising overexpression or underexpression of proteins, and wherein the retrieved information is identified and extracted using a service module configured to perform natural language processing and machine learning;

determining gene composition for the multigene panel selection based on the retrieved information, wherein gene composition is selected based on a risk of each gene, an established prediction of each gene, a financial cost for including each gene, a clinical guideline, and available clinical management for each gene;

apply the request to one or more from a group of the personalized data repository for the user and the supporting knowledge bases, wherein the personalized data repository includes genetic test results, health/clinical information, and insurance coverage, and wherein the knowledge bases include information pertaining to genetic tests and clinical guidelines;

integrate data from the applied request with results from service modules and perform one or more from a group of content search, variation interpretation, and report generation to produce results for the request;

update the personalized data repository and supporting knowledge bases to include the results of the request and health status results of the user, wherein the personalized data repository is updated by integrating and validating the results of the request using an extract, transform, and load process, and wherein updating the personalized data repository and supporting knowledge bases improves gene panel selection during future workflows; and trigger surveillance services based on one or more events, wherein updating the personalized data repository and supporting knowledge bases triggers the surveillance services, wherein the surveillance services generate a surveillance report in response to the triggering, and wherein the surveillance services include longitudinal health monitoring to identify a change in a health status of the user.

18. The computer program product of claim 17, wherein the instructions to determine the gene composition for the multigene panel selection cause the computer to determine gene composition for one of a basic panel and a multiple expansive panel based on the retrieved information; and wherein the instructions are further executable by the computer to cause the computer to:

perform services based on the determined panel including one or more from a group of: NGS sequencing and variant interpretation/clinical management, genetic screening/testing advice, gene panel updating, producing new guidelines, identifying new genes/variations, and identifying personal health status changes.

19. The computer product of claim 17, wherein the request comprises an environmental factor or a social factor or a genetic factor, and the instructions are further executable by the computer to cause the computer to:

apply the request to the personalized data repository, wherein the personalized data repository comprises the environmental factor or the social factor or the genetic factor for each of a population of users;

integrate data pertaining to the environmental factor or the social factor or the genetic factor for each of the population of users from the applied request with the results from the service modules; and analyze the integrated data to determine whether the environmental factor or the social factor or the genetic factor increases or decreases a prevalence of a disease in the population relative to a control population of users.

20. The computer program product of claim 17, wherein the instructions are further executable by the computer to cause the computer to:

send a notification to a user including results of triggering the surveillance services.

* * * * *